(12) United States Patent
Calvez et al.

(10) Patent No.: US 9,181,294 B2
(45) Date of Patent: Nov. 10, 2015

(54) NUCLEOSIDE ANALOGUES FOR THE TREATMENT OF A VIRAL INFECTION, AND METHOD FOR EVALUATING THE SENSITIVITY TO SAID TREATMENT

(71) Applicant: Universite Pierre et Marie Curie (Paris 6), Paris (FR)

(72) Inventors: Vincent Calvez, Paris (FR); Anne-Genevieve Marcelin, Paris (FR); Cathia Soulie, Paris (FR); Melanie Etheve-Quelquejeu, Choisy-le-Roi (FR); Matthieu Sollogoub, Paris (FR)

(73) Assignee: Universite Pierre Et Marie Curie (Paris 6), Paris (FR)

( * ) Notice: Subject to any disclaimer, the term of this patent is extended or adjusted under 35 U.S.C. 154(b) by 0 days.

(21) Appl. No.: 14/354,044

(22) PCT Filed: Oct. 23, 2012

(86) PCT No.: PCT/FR2012/052433
§ 371 (c)(1),
(2) Date: Apr. 24, 2014

(87) PCT Pub. No.: WO2013/060980
PCT Pub. Date: May 2, 2013

(65) Prior Publication Data
US 2014/0323425 A1     Oct. 30, 2014

(30) Foreign Application Priority Data
Oct. 24, 2011    (FR) ..................... 11 59622

(51) Int. Cl.
| | | |
|---|---|---|
| A01N 43/04 | (2006.01) |
| A61K 31/70 | (2006.01) |
| C07H 17/02 | (2006.01) |
| A61K 31/7052 | (2006.01) |
| A61K 31/706 | (2006.01) |
| A61K 31/7042 | (2006.01) |
| A61K 31/7064 | (2006.01) |
| C07D 487/04 | (2006.01) |
| A61K 31/7076 | (2006.01) |
| A61K 45/06 | (2006.01) |
| C12Q 1/70 | (2006.01) |

(52) U.S. Cl.
CPC .............. *C07H 17/02* (2013.01); *A61K 31/706* (2013.01); *A61K 31/7042* (2013.01); *A61K 31/7052* (2013.01); *A61K 31/7064* (2013.01); *A61K 31/7076* (2013.01); *A61K 45/06* (2013.01); *C07D 487/04* (2013.01); *C12Q 1/70* (2013.01)

(58) Field of Classification Search
None
See application file for complete search history.

(56) References Cited

U.S. PATENT DOCUMENTS

2003/0008841 A1    1/2003    Devos et al.

FOREIGN PATENT DOCUMENTS

| EP | 0 462 621 | 12/1991 |
|---|---|---|
| WO | WO-2005/084653 | 9/2005 |

OTHER PUBLICATIONS

Debarge et al. JOC (2011), vol. 76, pp. 105-126.*
Zhu, et al., "Novel synthetic approach to multibenzoylated nucleosides", Synthetic Communications, vol. 38, 2008.
Endo, et al., "Oxidation of N, N-dialkyl-2', 3', 5'—tri-0-acetyladenosine a with Ruthenium tetraoxide and a novel selective N-Monodealkylation sequence", Journal of Organic Chemistry, vol. 44, No. 21, 1979.
Dai, et al., "Efficient chemical synthesis of AppDNA by adenylation of immobilized DNA-5'—monophosphate", Organic Letters, vol. 11, No. 5, 2009.

* cited by examiner

*Primary Examiner* — Patrick Lewis
(74) *Attorney, Agent, or Firm* — Cesari and McKenna, LLP

(57) ABSTRACT

The present invention describes the use of nucleoside analogs for the treatment of viral infections, in particular of an HIV infection, and also compositions comprising at least one of these analogs, and a method for evaluating the sensitivity to said treatment.

19 Claims, 1 Drawing Sheet

NUCLEOSIDE ANALOGUES FOR THE TREATMENT OF A VIRAL INFECTION, AND METHOD FOR EVALUATING THE SENSITIVITY TO SAID TREATMENT

CROSS REFERENCE TO RELATED APPLICATIONS

This application is the National Stage of International Application No. PCT/FR2012/052433, filed on Oct. 23, 2012, which claims the benefit of French Application No. 1159622 filed on Oct. 24, 2011. The contents of both applications are hereby incorporated by reference in their entirety.

The present invention describes nucleoside analogues and the use thereof for the treatment of a viral infection, in particular a human acquired immunodeficiency virus (HIV) infection.

BACKGROUND OF THE INVENTION

The medicaments proposed in the treatment of HIV can be divided up into six classes: nucleoside (nucleotide) reverse transcriptase inhibitors [N(t)RTIs], non-nucleoside reverse transcriptase inhibitors [NNRTIs], protease inhibitors [PIs], integrase inhibitors [INIs], CCR5 antagonists, and fusion inhibitors.

The introduction of a highly active antiretroviral therapy as HIV treatment has made it possible to significantly reduce mortality and morbidity for patients suffering from HIV throughout the world. The initial treatments recommended for HIV infection include at least two medicaments known to belong to the nucleoside reverse transcriptase inhibitor class.

However, most of the compounds used pose toxicity problems, and they all encounter resistance problems. Consequently, a decrease in side effects and an improvement in dosages (for example administration, once a day, of fixed-dose combination pills), which would allow greater compliance by patients, would limit the emergence of resistant variants, and would thus improve the longevity and quality of life of patients, are sought.

There is therefore a need for novel antiviral molecules which are both well tolerated and effective and which also have novel mechanisms of action.

In this context, the inventors have demonstrated that a subfamily of benzoylated nucleoside analogues exhibits, surprisingly, an advantageous antiviral activity both on the native HIV virus and on the resist variants, while at the same time having very low toxicity.

SUMMARY OF THE INVENTION

The present invention relates to compounds of formula (I) for use in the treatment of a viral infection, in particular an infection with an HIV virus.

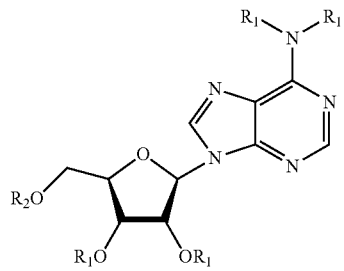

(I)

The present invention also relates to a pharmaceutical composition comprising at least one compound of formula (I) and a pharmaceutically acceptable support.

The present invention also provides an in vitro method for evaluating whether a patient infected with an HIV virus, in particular HIV-1, would be sensitive to a therapy with a compound as defined here, said method comprising searching for a mutation in codon 215 of the reverse transcriptase of the virus, a substitution of the wild-type threonine to tyrosine being indicative of a greater sensitivity to said compound, compared with the wild-type virus.

DETAILED DESCRIPTION OF THE INVENTION

Figure 1:
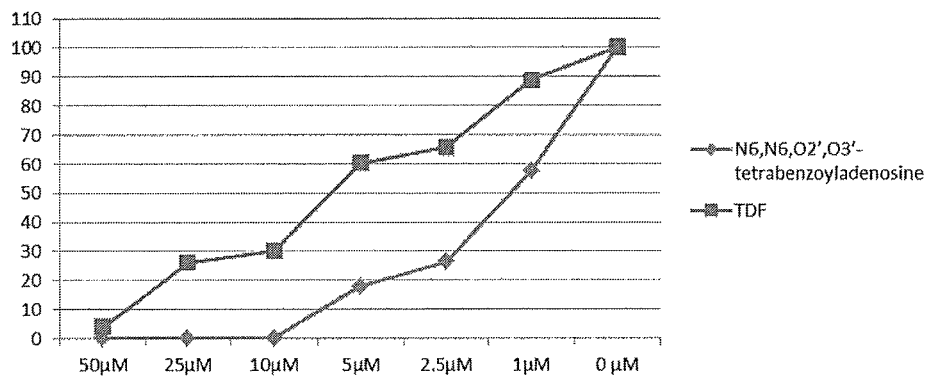
FIG. 1 is a graph showing the measurement of the IC50 (50% inhibitory concentration) of tetrabenzoyladenosine, compared with that of TDF (Tenofovir). The squares correspond to the Tenofovir and the diamonds to the tetrabenzoyladenosine ($N^6, N^6, O^{2'}, O^{3'}$-tetrabenzoyladenosine of formula A as described below).

The present invention relates to a compound of formula (I)

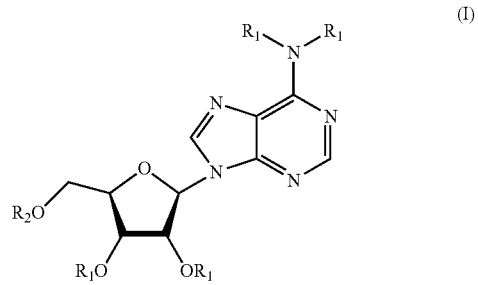

(I)

in which:

each R1 is independently chosen from a benzyl group and a benzoyl group (Bz), optionally substituted with one or more substituents chosen from a nitro group ($NO_2$), an alkyl group and a halogen atom;

R2 is chosen from a hydrogen atom, an acyl group, a monophosphate, diphosphate or triphosphate, or a stabilized phosphate derivative, an isomer, tautomer or enantiomer thereof, a prodrug or a pharmaceutically acceptable salt thereof, or a mixture thereof, for use in the treatment of a viral infection.

The virus may be, for example, HIV (human immunodeficiency virus), the hepatitis C virus (HCV), the hepatitis B virus or the herpes virus.

The compounds are particularly of use for treating a viral infection in patients infected with a viral strain carrying a mutation which confers thereon a resistance to the current treatments, for example a resistance to nucleoside or non-nucleoside reverse transcriptase inhibitors, or to integrase inhibitors or protease inhibitors, in particular with regard to HIV.

In particular, the viral infection is HIV.

All the genotypes are included, in particular the HIV-1, HIV-2 and HIV-O groups.

The compounds are of use for treating an infection in any patient. The compounds are more particularly effective for combating an infection with an HIV virus, in particular HIV-1, carrying the T215Y mutation.

Preferably one, preferably two, preferably three, and more preferentially the four R1 groups are benzoyl groups.

Preferably, R2 is chosen from a hydrogen atom, a group

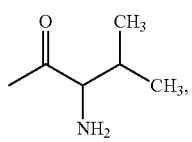

and a stabilized phosphate derivative chosen from a group

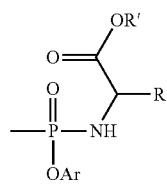

and a group

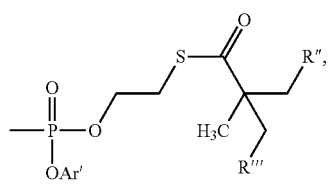

in which Ar and Ar' are phenyl or naphthyl groups optionally substituted with one or more halogen atoms, and R, R', R" and R'" are independently chosen from a hydrogen atom, a hydroxyl group (OH), an alkyl, a phenyl or an amine group NRaRb where Ra and Rb are chosen from hydrogen atoms, alkyls and haloalkyls.

Highly preferably, R2 is a hydrogen atom.

In the present invention, the term "alkyl group" denotes a linear, branched or cyclic hydrocarbon-based group comprising 1 to 8 carbon atoms, which is optionally substituted with at least one substituent chosen from halogen atoms, and hydroxyl (OH) and amino ($NH_2$) groups. By way of examples, mention may be made of methyl, ethyl, propyl, isopropyl, n-butyl, sec-butyl, pentyl, hexyl, cyclohexyl, heptyl and octyl groups.

In the present invention, the term "acyl group" denotes an alkyl group connected to the rest of the molecule by means of a C=O.

In the present invention, the term "stabilized phosphate derivative" denotes a group which is derived from a phosphate group and which makes it possible to form a stabilized nucleotide prodrug.

In the present invention, the term "halogen atom" denotes a chlorine, bromine, iodine or fluorine atom.

In the present invention, the term "haloalkyl" denotes an alkyl group as defined above, substituted with at least one halogen atom. By way of example, mention may in particular be made of the trifluoromethyl group.

In the present invention, the term "prodrug" of a compound of formula (I) denotes a compound which is converted into a corresponding monophosphorylated compound of formula (I) when it is administered in vivo, or which has the same activity by itself. In particular, mention may be made of the pharmaceutically acceptable salts and certain 5' derivatives, in particular hydrolyzable derivatives, of the active compounds.

In the present invention, the term "pharmaceutically acceptable salt" denotes a salt of a compound of formula (I) which has little or no undesired toxicological effect. It may, for example, be an acid addition salt such as a hydrochloride or an acetate, or a basic addition salt, such as a sodium or potassium salt.

A compound of formula (I) can be administered in stabilized prodrug form for example for improving its activity, its bioavailability or its stability or for modifying any undesired property of the compound of formula (I).

Among the compounds of the invention, the compound of formula A ($N^6,N^6,O^{2'},O^{3'}$-tetrabenzoyladenosine) is highly preferred.

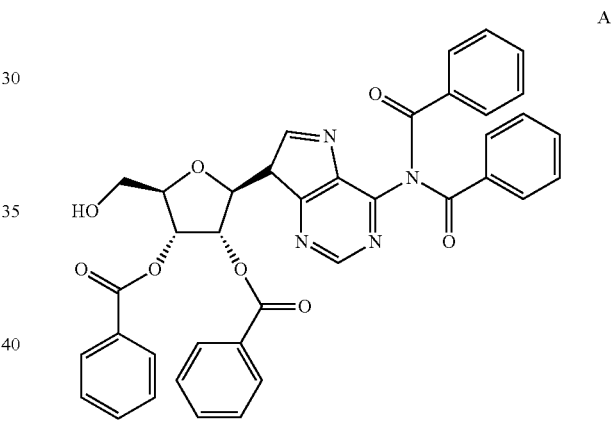

The $N^6,N^6,O^{2'},O^{3'}$-tetrabenzoyladenosine A can be synthesized as described initially by Khorana et al. (Lohrmann, R.; Khorana, H. G. *J. Am. Chem. Soc.* 1964, 86, 4188-4194), or using the process improved by Scott et al. (Zhu, X.-F.; Scott, A. I. *Synthetic Commun.* 2008, 1346-1354) using tert-butyldimethylsilyl as temporary 5'-OH protective group.

The inventors have demonstrated that $N^6,N^6,O^{2'},O^{3'}$-tetrabenzoyladenosine has a greater antiviral (in particular anti-HIV) activity than Tenofovir (TDF), which is the antiretroviral most widely used for the treatment of patients infected with HIV. The low level of cell toxicity measured makes employing this compound particularly useful in patients infected with HIV. In addition, without wishing to be bound to any mechanism of action, the inventors have demonstrated that this compound acts at an early stage of viral infection, namely before the integration of the virus into the DNA of the cell. More particularly, the inventors have shown an inhibition of proviral DNA production. This property of the compounds of the invention is particularly advantageous for an effective treatment, upstream of the cell integration.

The present invention also relates to a pharmaceutical composition comprising at least one compound of formula (I) and a pharmaceutically acceptable support.

In the context of the invention, the term "pharmaceutically acceptable support" denotes substances such as excipients, carriers, adjuvants, buffers which are conventionally used, in combination with the active ingredient(s), for the preparation of a medicament. The choice of such supports depends essentially on the route of administration envisaged.

In one particular embodiment, the compounds of the invention may be in encapsulated form, by being, for example, introduced into microspheres or microcapsules which are reservoirs consisting of a core of active ingredient surrounded by a membrane of coating material. The polymers forming the coating material may be of natural origin (gelatin, chitosan, etc.), semisynthetic origin (cellulose derivatives, etc.) or synthetic origin, such as the lactic and glycolic acid copolymers commonly used. The compounds of the invention may also be encapsulated in nanoparticles, which are colloidal systems of which the size is between 10 and 1000 nm, based on biodegradable polymers, or on lipids capable of retaining one or more active molecules by sequestration and/or adsorption.

The pharmaceutical composition according to the invention preferably comprises an amount of compound according to the invention of between 5 µg and 1000 mg, preferably between 1 and 500 mg, preferably between 5 and 100 mg.

The ratio between the amounts by weight of compound according to the invention and of pharmaceutically acceptable support is between 5/95 and 95/5, preferably between 20/80 and 80/20.

The compounds of the invention may be the only active ingredients, or they may be combined with other active ingredients. The pharmaceutical composition according to the invention may thus also comprise at least one other pharmaceutical active agent, in particular at least one other medicament used for the treatment of viral infection. In particular, the composition according to the invention may also comprise, or be combined with, one or more other antiretrovirals, for example Tenofovir. Generally, any antiretroviral may be combined, namely reverse transcriptase inhibitors, in particular nucleoside or nucleotide and non-nucleoside inhibitors, protease inhibitors, integrase inhibitors, entry inhibitors (anti-CCR5), fusion inhibitors, and inhibitors for attachment to the CD4 binding site. Among the antiretrovirals, use may, for example, be made of those which are currently commercially available, such as lamivudine, emtricitabine, zalcitabine, abacavir, zidovudine, didanosine, stavudine, adefovir, tenofovir, efavirenz, etravirine, nevirapine, delavridine, rilpivirine, amprenavir, fosamprenavir, tipranavir, lopinavir, ritonavir, indinavir, saquinavir, darunavir, atazanavir, nelfinavir, raltegravir, eviltegravir, dolutegravir, enfuvirtide or maraviroc.

The compounds or compositions according to the invention may be administered in various ways and in various forms. Thus, they may be administered systemically, orally, by inhalation or by injection, for instance intravenously, intramuscularly, subcutaneously, transdermally, intra-arterially, etc., intravenous, intramuscular, subcutaneous and oral administration and administration by inhalation being preferred. For the injections, the compounds are generally conditioned in the form of liquid suspensions, which can be injected by means of syringes or infusions, for example. In this regard, the compounds are generally dissolved in buffered, isotonic, physiological, saline, etc., solutions which are compatible with pharmaceutical use and known to those skilled in the art. Thus, the compositions may contain one or more agents or carriers chosen from dispersants, solubilizing agents, stabilizers, preservatives, etc. Agents or carriers which can be used in liquid and/or injectable formulations are, in particular, methylcellulose, hydroxymethylcellulose, carboxymethylcellulose, polysorbate 80, mannitol, gelatin, lactose, vegetable oils, acacia, etc.

The compounds can also be administered in the form of gels, oils, tablets, suppositories, powders, gel capsules, capsules, aerosols, etc., optionally by means of galenical forms or devices which provide prolonged and/or delayed release. For this type of formulation, an agent such as cellulose, carbonates or starches is advantageously used.

It is understood that the flow rate and/or the dose injected can be adjusted by those skilled in the art according to the patient, to the pathological condition concerned, to the mode of administration, etc. Typically, the compounds are administered at doses which can range between 0.1 µg and 100 mg/kg of body weight, more generally from 0.01 to 10 mg/kg, typically between 0.1 and 10 mg/kg. Generally, between 5 µg and 1000 mg, preferably between 1 and 500 mg, preferably between 5 and 100 mg per day are administered. In addition, repeated injections can be carried out, as appropriate. Furthermore, for chronic treatments, delayed or prolonged systems can be used.

The present invention also relates to a method for treating a viral infection, comprising the administration, to a patient, of an effective amount of at least one compound of formula (I) and/or of a composition containing same.

A subject of the present invention is also the use of at least one compound as defined above, in the context of the preparation of a pharmaceutical composition intended for the treatment of a viral infection.

For personalized medicine purposes, a subject of the invention is also a method for identifying patients infected with an HIV virus, in particular HIV-1, who would be very sensitive to a therapy with a pharmaceutical composition described here, said method comprising searching for a mutation in codon 215 of the reverse transcriptase, a substitution of the wild-type threonine to tyrosine being indicative of a greater sensitivity to a compound of the invention, compared with a wild-type virus. The term "patients who are very sensitive" is intended to mean patients for whom a therapy with a compound of the invention would be particularly advantageous, given that the compounds of the invention remain also useful for treating an infection with a wild-type virus or a virus carrying other mutations.

The search for this mutation can be carried out by any standard technique of genotyping, sequencing or rapid detection with probes (cf. for example, Ross, et al AIDS Research and Human Retroviruses, 1999, 15(14): 1287-1292; Mitsuya et al, J Virol. 2008, 82(21):10747-55).

In the context of the invention, the term "treatment" denotes the preventive, curative or palliative treatment and also the management of patients (reduction of suffering, improvement of life span, slowing of the progression of the disease, etc.). The treatment can also be carried out in combination with other chemical or physical agents or treatments. The compounds according to the invention are preferably conditioned and administered in combined, separate or sequential manner with respect to other therapeutic agents or treatments. The treatments and medicaments of the invention are quite particularly intended for human beings. The patients capable of being treated with the compounds and/or compositions of the invention can in particular be a population of patients resistant to the antivirals conventionally used for the treatment of the viral infection, in particular of patients (preferably patients infected with the HIV virus) resistant to nucleoside or non-nucleoside reverse transcriptase inhibitors, or to integrase or protease inhibitors.

The nucleoside reverse transcriptase inhibitors comprise, in particular, the following molecules: zidovudine, a molecule also known as AZT, lamivudine, emtricitabine, didanosine, stavudine, abacavir, zalcita bine, tenofovir, racivir, amdoxovir, apricitabine, elvucitabine.

The non-nucleoside reverse transcriptase inhibitors comprise, in particular, the following molecules: efavirenz, nevirapine, etravirine, delavirdine, rilpivirine.

The integrase inhibitors include elvitegravir and dolutegravir.

The protease inhibitors include the following molecules: amprenavir, tipranavir, indinavir, saquinavir, fosamprenavir, ritonavir, darunavir, atazanavir, nelfinavir.

The compounds according to the invention can be synthesized simply (in 3 steps only) from, for example, commercial adenosine.

The three steps are carried out without any intermediate purification step; this involves first of all a step of regioselective protection of the 5'-position of the adenosine using tert-butyldimethylsilyl chloride, followed by protection of the amine function of the base and of the other two hydroxyls in the 2'- and 3'-position of the ribose, with benzoyl chloride. The terminal step is the deprotection of the hydroxyl in the 5'-position, which can be carried out with tetrabutylammonium fluoride or trifluoroacetic acid, preferably trifluoroacetic acid. A purification step using a chromatography column then makes it possible to obtain the compound of interest.

Other aspects and advantages of the present application will emerge upon reading the examples which follow, which should be considered to be non-limiting illustrations.

EXAMPLES

Example 1

Synthesis of the Compound $N^6,N^6,O^{2'},O^{3'}$-tetrabenzoyladenosine (Compound A) according to the Invention Example 1.1

First Embodiment tert-Butyldimethylsilyl chloride (TBSCl) (396 mg, 2.6 mmol) is added, at 0° C., to a solution of commercial adenosine (540 mg, 2.0 mmol) and of pyridine (10 ml). After stirring for 2 h at 0° C., the reaction mixture is brought back to ambient temperature and stirred again for 7 h. The solution is then cooled to 0° C. and benzoyl chloride (1.12 ml, 9.6 mmol) is added dropwise. After stirring overnight at ambient temperature, the mixture is diluted in $CH_2Cl_2$ (100 ml) and washed with a saturated solution of NaCl (40 ml). The aqueous phase is extracted with $CH_2Cl_2$ (2×40 ml), and the organic phases are combined, dried over $Na_2SO_4$, filtered and concentrated under vacuum. The reaction crude obtained is dissolved in THF (36 ml), and an aqueous solution of trifluoroacetic acid TFA (18 ml, TFA/$H_2O$ 1:1) is slowly added. After stirring for 3 h at ambient temperature, the reaction mixture is neutralized with a solution of $NaHCO_3$ (9.72 g in 100 ml of $H_2O$) at 0° C. and extracted with $CH_2Cl_2$ (4×50 ml). The organic phases are combined, dried over $Na_2SO_4$, and concentrated under vacuum after filtration.

The product obtained is purified on a chromatography column (eluent: cyclohexane/EtOAc=4:1 to 1:1 then $CH_2Cl_2$/$CH_3OH$ 100:5) to give tetrabenzoyladenosine in the form of a white solid. Yield: 1.36 g (99%).

Example 1.2

Second Embodiment tert-Butyldimethylsilyl chloride (TBSCl) (2.2 g, 14.6 mmol) is added, at 0° C., to a solution of commercial adenosine (3 g, 11.2 mmol) and of distilled pyridine (60 ml). After stirring for 4 h at 0° C., the reaction mixture is brought back to ambient temperature and stirred again overnight. The pyridine is evaporated off and then the reaction mixture is taken up in $CH_2Cl_2$ (500 ml) and MeOH (50 ml), and washed with a saturated solution of NaCl (500 ml) and of $NaHCO_3$ (500 ml). The aqueous phase is extracted with $CH_2Cl_2$ (200 ml), and the organic phases are combined, dried over $Na_2SO_4$, filtered and concentrated under vacuum. The solid is dissolved in 60 ml of pyridine, the solution is cooled to 0° C. and benzoyl chloride (6.26 ml, 53.9 mmol) is added dropwise. After stirring overnight at ambient temperature, the mixture is diluted in $CH_2Cl_2$ (300 ml) and washed with a saturated solution of NaCl (2×150 ml). The aqueous phase is extracted with $CH_2Cl_2$ (150 ml), and the organic phases are combined, dried over $Na_2SO_4$, filtered and concentrated under vacuum. The reaction crude obtained is dissolved in THF (100 ml), and an aqueous solution of trifluoroacetic acid TFA (50 ml, TFA/$H_2O$ 1:1) is slowly added. After stirring overnight at ambient temperature, the reaction mixture is neutralized with a solution of $NaHCO_3$ at 0° C. and extracted with $CH_2Cl_2$ (2×150 ml). The organic phases are combined, dried over $Na_2SO_4$, and concentrated under vacuum after filtration.

The product obtained is purified on a chromatography column (eluent: cyclohexane/EtOAc=4:1 to 1:1 then $CH_2Cl_2$/$CH_3OH$ 100:5) to give tetrabenzoyladenosine in the form of a white solid. Yield: 5.96 g (77%).

Characterization of the Product Obtained with the Two Embodiments

Rf: 0.25 (cyclohexane/EtOAc=2:1); $^1$H NMR: (CDCl$_3$) δ 8.70 (s, 1H, H2 or H8), 8.21 (s, 1H, H2 or H8), 8.05 (d, J=7.5 Hz, 2H, Bz), 7.33-7.86 (m, 18H, Bz), 6.36 (m, 2H, H1', H2'), 6.06 (dd, J=1.6, 5.2 Hz 1H, H3'), 5.56 (bs, 1H, OH), 4.64 (bs, 1H, H4'), 4.05 (m, 2H, 2×H5')

HRMS: calculated for $C_{38}H_{29}N_5O_8Na$: 706.1914. found 706.1917 [M+Na+].

Example 2

Antiviral and Cytotoxicity Tests

Materials and Methods:
Compounds:
Compound A (tetrabenzoyladenosine, cf. preparation in example 1) is dissolved in DMSO (dimethyl sulphoxide) at 10 mM. Commercial Tenofovir is dissolved in water at 1 g/l.
Cells and Viruses:
HeLa-P4 cells are HeLa CD4 LTR-LacZ cells in which the expression of LacZ is induced by the trans-activating Tat protein of HIV, making it possible to precisely quantify the HIV-1 infectivity from a single replication cycle. HeLa-CD4 cells growing exponentially at a density of 1×10$^4$/ml are placed in 96-well plates and infected on the following day with 3 ng of HIV p24 antigen in the presence of various concentrations of compounds.
Antiviral Test in HeLa-P4 Cells
The titres for a single cycle of the virus were determined in HeLa-P4 cells. The cells were infected, in duplicate, in 96-well plates, with the HIV-1 pNL-4.3 clone (equivalent to 3 ng of p24 antigen). The titres for a single cycle of the viruses were determined 48 hours after infection by quantifying the beta-galactosidase activity in P4 lysates by means of a colorimetric test (CPRG test) based on cleavage of chlorophenol red-beta-D-galactopyranoside (CPRG) by beta-galactosidase. The 50% inhibitory concentration (IC50) was determined as the concentration of compound A providing 50% inhibition of beta-galactosidase levels compared with the untreated infected cells.

Antiviral Test in MT2 Cells

The MT2 cells were concentrated at $3 \times 10^6$/ml and infected with $10^7$ viruses (LAI). The cells were distributed into 96-well plates ($1 \times 10^5$/well) and incubated in the presence of various concentrations of compound A (in quadruplicate). The viral loads were determined on day 3 (Cobas AmpliPrep/Cobas TaqMan (CTM) HIV-1 v2 test).

Cytotoxicity Tests

A cell viability test measuring the absorbance at 560 and 690 nm using the yellow tetrazolium MTS [3-(4,5-dimethyl-2-thiazolyl)-2,5-diphenyltetrazolium bromide] reagent was carried out with the tetrabenzoyladenosine in the HeLa-CD4, Vero, FH, MT2 and SupT1 cell lines.

Results

Antiviral Activity Towards HIV

The antiviral activity of compound A according to the invention was evaluated using an amount of HIV corresponding to 3 ng of p24 antigen. Presented here for comparison is the activity obtained with a compound which does not have a double benzoylation in the N6 position.

| Structure | Viral production (10 µM of compound) |
|---|---|
| compound A (NBz₂, HO-ribose-BzO, OBz) | 0% |
| (NHBz, HO-ribose-BzO, OBz) | 109% |

Using an amount of HIV corresponding to 3 ng of p24 antigen, the IC50 of the tetrabenzoyladenosine (compound A) is between 1 and 2 µM. Under the same conditions, the IC50 of TDF (Tenofovir) is between 5 and 10 µM (see FIG. 1).

Compound A according to the invention was tested on the pNL4-3 virus optionally modified by site-directed mutagenesis, comprising or not comprising (wt) the mutations located in the reverse transcriptase gene and associated with resistance to the main NRTIs used in clinical practice. Tables 1A to 1C below group together the resistance indices of compound A according to the invention on the viruses with and without mutation.

The resistance index of a mutant represents the ratio of the concentration of compound capable of inhibiting by half (IC50) the growth of the mutant virus tested, to the concentration of compound capable of inhibiting by half (IC50) the growth of the wild-type virus.

A resistance index less than or equal to 1 signifies that the viral strain tested is sensitive to the treatment, or in other words, that the compound effectively inhibits the multiplication of the virus. A resistance index greater than approximately 1.5 or 2 signifies that the viral strain is resistant to the treatment.

TABLE 1A

Resistance index (fold change) of the mutants with respect to the nucleoside reverse transcriptase inhibitors

|  | Resistance index |
|---|---|
| pNL4-3 wild type | 1 |
| pNL4-3 T215Y | 0.41 |
| pNL4-3 M41L-L210W-T215Y | 0.38 |
| pNL4-3 M184V | 0.99 |
| pNL4-3 K65R | 0.92 |
| pNL4-3 K65R-M184V | 1.07 |
| pNL4-3 M184V-M41L-L210W-T215Y | 0.58 |

Compound A was tested on MT2 cells infected with LAI viruses. The IC50 was determined in this case to be 1.6 µM.

TABLE 1B

Resistance index of the mutants with respect to the non-nucleoside reverse transcriptase inhibitors

|  | Resistance index |
|---|---|
| pNL4-3 wild type | 1 |
| pNL4-3 K103N | 1 |
| pNL4-3 E138K | 0.89 |

TABLE 1C

Resistance index of the mutants with respect to the integrase inhibitors

|  | Resistance index |
|---|---|
| pNL4-3 wild type | 1 |
| pNL4-3 N155H | 1.04 |
| pNL4-3 G140S-Q184H | 0.99 |
| pNL4-3 Q184H | 0.88 |

All the resistant mutants are sensitive to compound A, and some of them are even more sensitive (resistance index <1), such as, in particular, those carrying the T215Y mutation.

Cytotoxicity Assay

Using various cell types (HeLa-CD4, Vero, FH, MT2 and SupT1), the CC50 (50% cytotoxic concentration) of compound A was measured at more than 100 µM in all cases.

Example 3

Inhibition of Double-Stranded Proviral DNA Production and of Cellular RNA Production The MT2 cells were concentrated at $15 \times 10^6$/ml and incubated for 2 h with 10 or 25 µM of compound A. The Lai virus is then added at a multiplicity of infection of 0.01 for 1 h. The cells are washed and then incubated in culture medium containing 10 or 25 μM of the compound to be tested. A sample of 1×10^6 cells is taken at various times and the viral DNA is quantified by means of a Taqman real-time PCR method. The viral RNA loads are quantified in the culture medium (Cobas AmpliPrep/Cobas TaqMan (CTM) HIV-1 v2 test).

Figure 2:
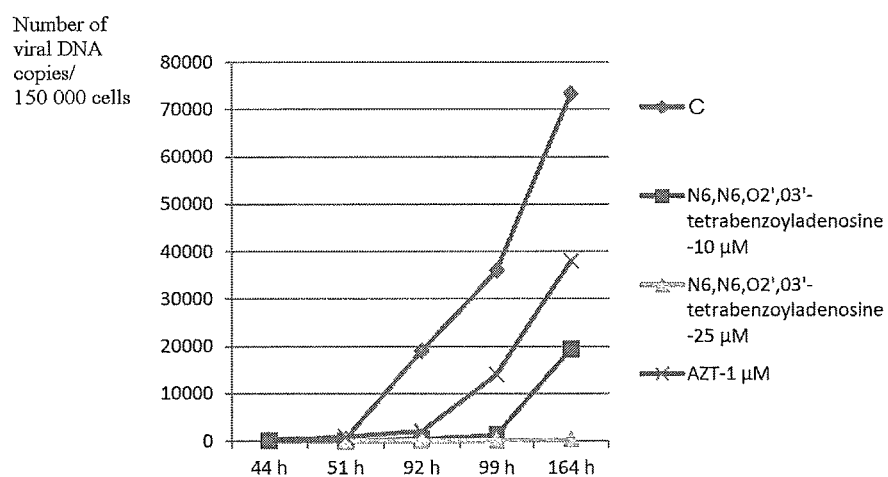
FIG. 2 is a graph showing the number of viral DNA copies for 150 000 infected MT2 cells, as a function of time (C=control, AZT=zidovudine).
Figure 3:
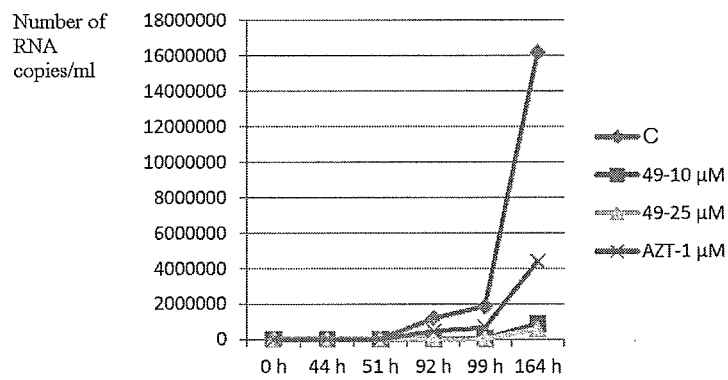
FIG. 3 is a graph showing the number of viral RNA copies per ml of infected MT2 cells, as a function of time (C=control, AZT=zidovudine).

The results are given in FIGS. 2 and 3. They show that the appearance of the intracellular viral DNA (FIG. 2) and the production of the extracellular viral RNA (FIG. 3) are inhibited by compound A. In other words, compound A prevents intracellular viral DNA production and, consequently, extracellular RNA production. The comparison with AZT (zidovudine) shows the clear superiority of compound A on inhibition of the viral load.

The invention claimed is:

1. A method for treating a viral infection in a patient, which method comprises administering a patient with a compound of formula (I)

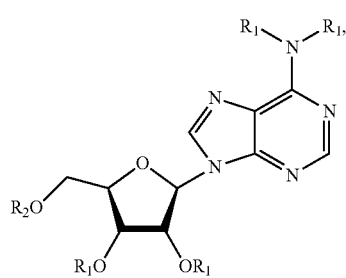

in which:
each $R_1$ is independently chosen from a benzyl group and a benzoyl group, optionally substituted with one or more substituents chosen from a nitro group ($NO_2$), an alkyl group and a halogen atom, and
$R_2$ is selected from a group consisting of a hydrogen atom, an acyl group, a monophosphate, diphosphate or triphosphate, and a stabilized phosphate derivative,
an isomer, tautomer or enantiomer thereof, a prodrug or a pharmaceutically acceptable salt thereof, or a mixture thereof.

2. The method according to claim 1, wherein the viral is selected from the group consisting of an infection with the HIV virus, the hepatitis C virus, the hepatitis B virus and the herpes virus.

3. The method according to claim 1 wherein the infection is an infection with the HIV virus.

4. The method according to claim 3, wherein the infection is an infection with the HIV-1 virus.

5. The method according to claim 3 wherein the patient is a patient infected with the HIV virus and resistant to nucleoside reverse transcriptase inhibitors.

6. The method according to claim 1, wherein the four $R_1$ groups are benzoyl groups.

7. The method according to claim 1, wherein $R_2$ is a stabilized phosphate derivative chosen from a group

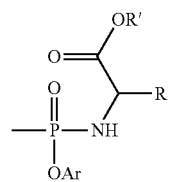

and a group

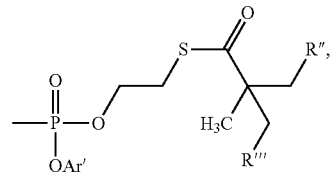

in which Ar and Ar' are phenyl or naphthyl groups optionally substituted with one or more halogen atoms, and R, R', R" and R'" are independently selected from the group consisting of a hydrogen atom, a hydroxyl group (OH), an alkyl, a phenyl, and an amine group NRaRb where Ra and Rb are chosen from hydrogen atoms, alkyls and haloalkyls.

8. The method according to claim 1, wherein $R_2$ is a hydrogen atom.

9. The method according to claim 8, wherein the compound is $N^6,N^6,O^{2'},O^{3'}$-tetrabenzoyladenosine.

10. A pharmaceutical composition, comprising at least a compound of formula (I)

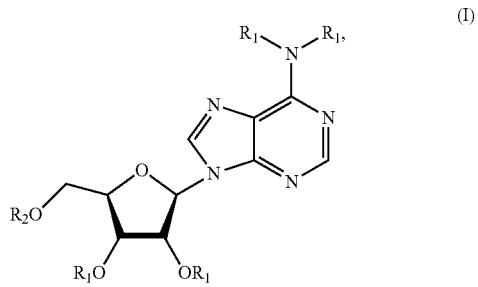

in which:
each $R_1$ is independently chosen from a benzyl group and a benzoyl group, optionally substituted with one or more substituents chosen from a nitro group ($NO_2$), an alkyl group and a halogen atom, and
$R_2$ is selected from the group consisting of a hydrogen atom, an acyl group, a monophosphate, diphosphate or triphosphate, and a stabilized phosphate derivative,
an isomer, tautomer or enantiomer thereof, a prodrug or a pharmaceutically acceptable salt thereof, or a mixture thereof, and
a pharmaceutically acceptable support.

11. The composition according to claim 10, in which the compound of formula (I) is $N^6,N^6,O^{2'},O^{3'}$-tetrabenzoyladenosine.

12. The composition according to claim 10, further comprising one or more other antiretrovirals.

13. The composition according to claim 10, wherein the composition is suitable for oral administration.

14. An In vitro method for evaluating whether a patient infected with an HIV virus, in particular HIV-1, would be sensitive to a therapy with a compound as defined in claim 1, said method comprising searching for a mutation in codon 215 of the reverse transcriptase of the virus, a substitution of the wild-type threonine to tyrosine being indicative of a greater sensitivity to said compound compared with the wild-type virus.

15. The method according to claim 2 wherein the infection is an infection with the HIV virus.

16. The composition according to claim 11 further comprising one or more other antiretrovirals.

17. The composition according to claim 11 wherein the composition is suitable for oral administration.

18. The composition according to claim 12 wherein the composition is suitable for oral administration.

19. The composition according to claim 16 wherein the composition is suitable for oral administration.

* * * * *